United States Patent
Zenobia et al.

(10) Patent No.: US 11,573,228 B2
(45) Date of Patent: Feb. 7, 2023

(54) BIOMARKERS OF NEUTROPHIL DEREGULATION AS DIAGNOSTIC FOR GINGIVITIS

(71) Applicant: Colgate-Palmolive Company, New York, NY (US)

(72) Inventors: Camille Zenobia, Hampton, NJ (US); Harsh Mahendra Trivedi, Hillsborough, NJ (US); Ying Yang, Monmouth Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/309,892

(22) PCT Filed: Dec. 17, 2019

(86) PCT No.: PCT/US2019/066813
§ 371 (c)(1),
(2) Date: Jun. 28, 2021

(87) PCT Pub. No.: WO2020/139620
PCT Pub. Date: Jul. 2, 2020

(65) Prior Publication Data
US 2022/0146512 A1    May 12, 2022

Related U.S. Application Data

(60) Provisional application No. 62/785,167, filed on Dec. 26, 2018.

(51) Int. Cl.
| | | |
|---|---|---|
| *G01N 33/50* | (2006.01) | |
| *G01N 33/68* | (2006.01) | |
| *G01N 33/569* | (2006.01) | |

(52) U.S. Cl.
CPC ... *G01N 33/56955* (2013.01); *G01N 33/5008* (2013.01); *G01N 33/6863* (2013.01); *G01N 2333/522* (2013.01); *G01N 2333/523* (2013.01)

(58) Field of Classification Search
None
See application file for complete search history.

(56) References Cited

U.S. PATENT DOCUMENTS

| | | | |
|---|---|---|---|
| 5,736,341 A * | 4/1998 | Sorsa | C07K 16/40 436/523 |
| 2014/0205613 A1 | 7/2014 | Voss et al. | |
| 2018/0320217 A1* | 11/2018 | Haught | C12Q 1/32 |

FOREIGN PATENT DOCUMENTS

| | | |
|---|---|---|
| JP | 2018-072163 | 5/2018 |
| WO | 2018005335 | 1/2018 |

OTHER PUBLICATIONS

International Search Report and the Written Opinion of the International Searching Authority issued in International Application PCT/US2019/066813 dated Apr. 22, 2020.
Muller et al., 2016, "Salivary pellets induce a pro-inflammatory response involving the TLR4-NF-kB pathway in gingival fibroblasts", BMC Oral Health,17(1).
Bamashmous, S. (2019) "Investigation of Chemokine and Microbiome Profiles in Gingival Health and Disease in Humans", (Dissertation) University of Washington: 167 pages.
Calandra T, Roger T. Macrophage migration inhibitory factor: a regulator of innate immunity. Nature Reviews Immunology Oct. 3, 2003:791-800.
Deinzer R, Weik U, Kolb-Bachofen V, Herforth A. Comparison of experimental gingivitis with persistent gingivitis: differences in clinical parameters and cytokine concentrations. J Periodont Res 2007 318-324.
Nonnenmacher C, Helms K, Bacher M, Nüsing RM, Susin C, Mutters R, Flores-de-Jacoby L, Mengel R. Effect of age on gingival crevicular fluid concentrations of MIF and PGE2. J Dent Res. Jul. 2009 88(7):639-43.
Offenbacher S, Barros S, Mendoza L, Mauriello S, Preisser J, Moss K, de Jager M, Aspiras M. Changes in gingival crevicular fluid inflammatory mediator levels during the induction and resolution of experimental gingivitis in humans. J Clin Periodontol. Apr. 2010 37(4):324-33.
Sadik CD, Kim ND, Luster AD. Neutrophils cascading their way to inflammation. Trends Immunol. Oct. 2011 32(10):452-60.
Tatakis DN, Trombelli L. Modulation of clinical expression of plaque-induced gingivitis. J Clin Periodontol. 2004 31(4):229-238.

\* cited by examiner

*Primary Examiner* — Elizabeth C. Kemmerer

(57) ABSTRACT

Methods of determining one or more ratios of chemokines in gingival crevicular fluid of an individual selected from the group consisting of: MIF:MIP1a, MIF:CXCL1; MIF:CXCL5; M1F:CXCL8; MIF:CXCL2; and MIF:CXCL6 and methods of identifying an individual as having gingivitis comprising determining one or more ratios of the chemokines in gingival crevicular fluid are disclosed. Methods of treating individuals who are identified as having gingivitis by determining one or more ratios of the chemokines in gingival crevicular fluid are disclosed. Also disclosed are methods of monitoring the treatment individuals who have gingivitis.

12 Claims, 4 Drawing Sheets

BIOMARKERS OF NEUTROPHIL DEREGULATION AS DIAGNOSTIC FOR GINGIVITIS

BACKGROUND

The gums, also referred to as gingiva, which are part of the soft tissue lining of the mouth, surround the teeth and provide a seal around them. The gingival margin is the interface between the sulcular epithelium and the epithelium of the oral cavity. This interface exists at the most coronal point of the gingiva, otherwise known as the crest of the marginal gingiva. The gingival crevice, also called gingival sulcus, is the space located around a tooth between the wall of the unattached gum tissue and the enamel and/or cementum of the tooth.

Gingivitis is an inflammation of the gums that is the initial stage of gum disease. The direct cause of gingivitis is plaque—the soft, sticky, colorless film of bacteria that forms constantly on the teeth and gums. If the plaque is not removed by daily brushing and flossing, it produces toxins that can irritate the gum tissue, causing gingivitis. At this early stage in gum disease, damage can be reversed, since the bone and connective tissue that hold the teeth in place are not yet affected. Left untreated, however, gingivitis can become an advanced stage of gum disease, periodontitis, and cause permanent damage to teeth and jaw.

Healthy gums are firm and pale pink and fitted tightly around the teeth. At first, gingivitis may be undetectably by visual inspection but as it progresses symptoms become more apparent. Classic signs and symptoms of gingivitis include red, swollen, tender gums that may bleed when brushing or flossing. Another sign of gum disease is gums that have receded or pulled away from teeth, giving teeth an elongated appearance. Gum disease can cause pockets to form between the teeth and gums, where plaque and food debris collect. Some people may experience recurring bad breath or a bad taste in their mouth, even if the disease is not advanced.

Gingivitis is much more easily treated compared to periodontitis and can be resolved with good oral hygiene, such as longer and more frequent brushing, flossing and the use of an antiseptic mouthwash. The earlier gingivitis is treated the less chance of permanent damage. Accordingly, methods of diagnosing gingivitis during early stages of gingivitis allow for treatment to be initiated before the condition advances. Such methods can also be adapted to monitoring oral health and treatment over time.

BRIEF SUMMARY

Biomarkers have been identified that indicate neutrophil deregulation associated with gingivitis. Methods of diagnosing gingivitis, methods of monitoring oral health and response to treatment for gingivitis, methods of identifying and evaluating compounds and compositions which modulate neutrophil deregulation associated with gingivitis and are useful in the treatment of gingivitis are provided in which the biomarkers levels are measured.

DETAILED DESCRIPTION

Figure 1:
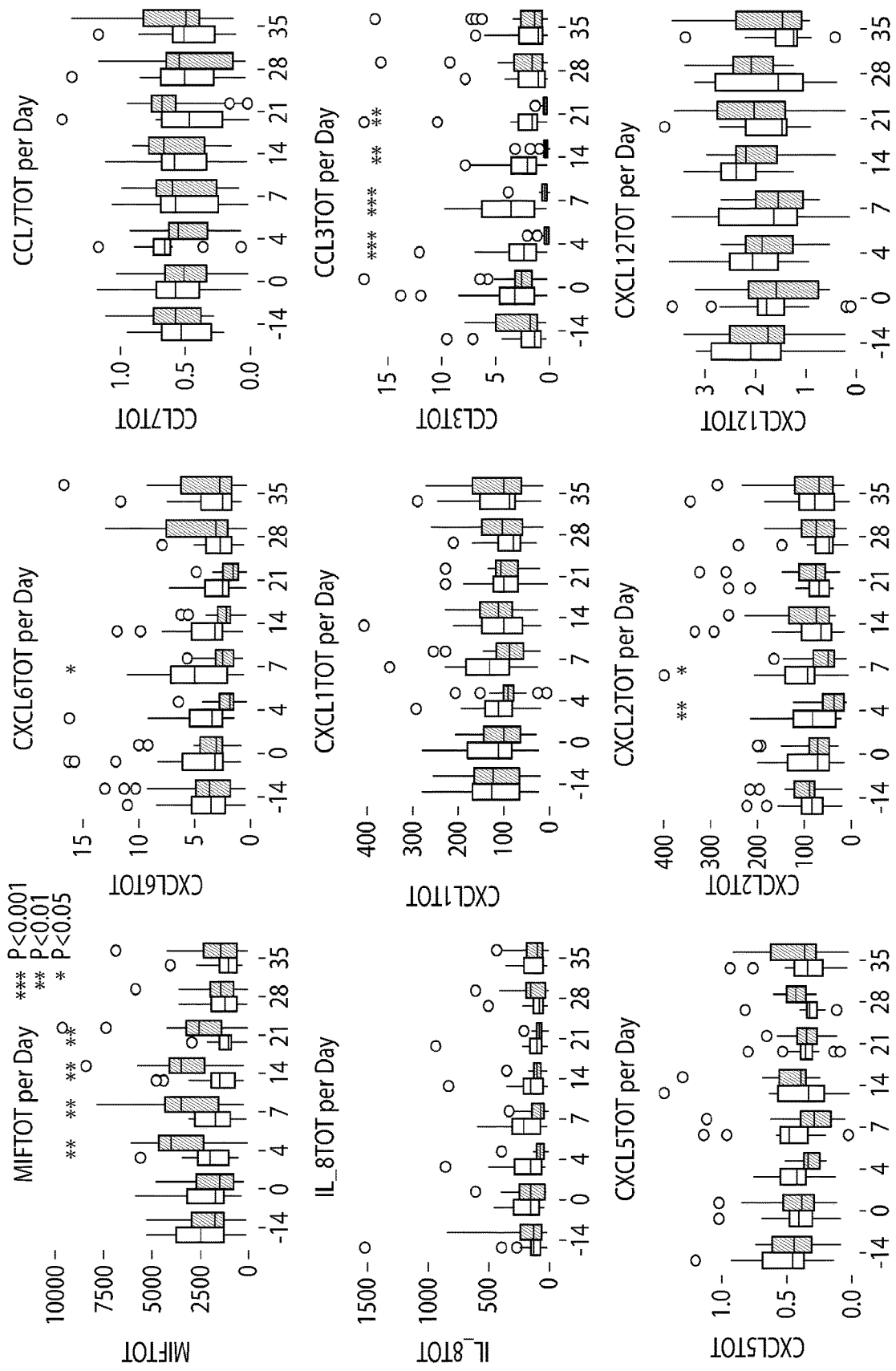
FIG. 1 shows control and test data side by side in bar graphs for the chemokines measured from Example 1.

Gingival crevicular fluid (GCF) is an inflammatory exudate that can be collected at the gingival margin or within the gingival crevice. The methods referred to herein relates to biochemical analyses of the fluid as a noninvasive means of assessing oral health, diagnosing gingivitis in an individual with early stage gingivitis, confirming the diagnosis of an individual suspected of having gingivitis, monitoring oral health of an individual and monitoring responses to treatment in individuals being treated for gingivitis.

Early detection of gingivitis allows for treatment and resolution before symptoms appear and damage occurs. The methods provided herein provide tools to proactively maintain good gum health and more effectively minimize and solve gum problems. The methods thereby are useful in efforts to control inflammation and maintain a healthy pink, pain free mouth. The methods herein are part of an overall oral health tool kit useful to quiet inflamed gums and to aid in efforts toward an active, healthy lifestyle.

Chemokines MIF, MIP1a, CXCL1, CXCL5, CXCL8, CXCL2 and CXCL6, among others, are present in gingival crevicular fluid of an individual. Neutrophils are primary defense cells in gingival tissue. Individuals with gingivitis, even at very early stages of the condition, experience neutrophil recruitment to affected areas including the gingival crevice. With the increased presence of neutrophils, there are changes to the local environment such as changes to the quantity of these chemokines present.

Chemokine levels in the area where plaque forms can vary greatly from person to person. That is, there is a wide baseline of protein production from person to person, whether such person has healthy gums or gingivitis. Accordingly, baseline variation makes use of chemokine levels as a diagnostic is difficult since quantity ranges indicative of healthy gums and quantity ranges indicative gingivitis cannot be accurately established.

Methods of identifying and monitoring gingivitis have been developed that eliminate baseline issues by employing chemokine ratio instead. The use of ratios minimizes the issues that arise due to baseline variance. Regardless of baseline, a substantial increase in the level of the chemokine MIF in the gingival crevicular fluid, coupled with broad reductions in the levels of the chemokines MIP-1a, CXCL1, CXCL5, CXCL8, CXCL2 and CXCL6 is characteristic of gingivitis. Thus, neutrophil chemokine deregulation an assessed in gingival crevicular fluid as a measure of gingivitis by using the patterning of chemokines as a diagnostic indicator of gingivitis. That is, the increase in MIF levels and decrease in MIP-1a, CXCL1, CXCL5, CXCL8, CXCL2 and CXCL6 levels in the GCF provides an opportunity for diagnosis based upon the ratios MIF:MIP-1a, MIF:CXCL1, MIF:CXCL5, MIF:CXCL8, MIF:CXCL2 and MIF:CXCL6 wherein increased ratios are indicative of gingivitis.

Methods provided herein include quantifying chemokine levels, including MIF and one or more additional chemokines selected from the group MIP-1a, CXCL1, CXCL5, CXCL8, CXCL2 and CXCL6, in the gingival crevice and calculating one or more of the ratios MIF:MIP-1a, MIF:CXCL1, MIF:CXCL5, MIF:CXCL8, MIF:CXCL2 and MIF:CXCL6.

Chemokines in the GCF may be quantified using GCF samples obtained from the individual. There are three widely practiced methods to collect the GCF. The most used method for GCF collection is made with specifically designed absorbent filter paper as endodontic paper points or periopapers. The endodontic paper points or periopapers are inserted into the gingival crevice and left in situ for 5 to 60 seconds, usually 30 seconds, to allow the GCF to be adsorbed by the paper. The GCF is eluted from the endodontic paper points or periopapers in saline. Another GCF collection method, the gingival washing technique, consists of perfusing the GCF with an isotonic solution, as Hank's balanced solution, with fixed volume. The fluid collected represents a dilution of crevicular fluid, containing cells and soluble constituents, as plasma proteins. A third GCF collection method is inserting capillary tubes, with specific diameter, into the entrance of the gingival crevice and the fluid migrates into the tube by capillary action. The GCF that are collected may be evaluated for neutrophil chemokine deregulation indicative of gingivitis.

The collected GCF may be analyzed to measure the quantity of MIF and one or more of MIP-1a, CXCL1, CXCL5, CXCL8, CXCL2 and CXCL6 using commercially available kits. Examples of such kits FlowCytomix™ kits from eBioscience® (formerly Bender MedSystems®, flow cytometry, non-magnetic beads), the Human Cytokine panel from Invitrogen™ (Luminex®, non-magnetic beads), the Bio-Plex Pro™ X-Plex Custom Assay from Bio-Rad® (Luminex®, magnetic beads) and (iv) the MILLIPLEX® Kit from Millipore™ (Luminex®, magnetic beads). Multiplex kits with magnetic beads (Luminex®) from Invitrogen™ and BD™ Cytometric Bead Array (CBA) Human Enhanced Sensitivity kits (flow cytometry, non-magnetic beads) can be used.

MIF levels in the sample are quantified. In addition, levels are quantified of one or more additional chemokines selected from the group consisting of: MIP1a, CXCL1, CXCL5, CXCL8, CXCL2 and CXCL6 are also quantified. In some embodiments, MIF levels are quantified and one additional chemokines selected from the group consisting of: MIP1a, CXCL1, CXCL5, CXCL8, CXCL2 and CXCL6 are also quantified. In some embodiments, MIF levels are quantified and two, three, four, five or six additional chemokines selected from the group consisting of: MIP1a, CXCL1, CXCL5, CXCL8, CXCL2 and CXCL6 are also quantified. The following combinations of MIF and additional chemokines are quantified and ratio are calculated:

TABLE 1

Combinations of MIF plus one-six additional chemokines

| Chemokine levels quantified | Ratios calculated |
|---|---|
| Two chemokines measured | |
| MIF + MIP1a | MIF:MIP1a |
| MIF + CXCL1 | MIF:CXCL1 |
| MIF + CXCL5 | MIF:CXCL5 |
| MIF + CXCL8 | MIF:CXCL8 |
| MIF + CXCL2 | MIF:CXCL2 |
| MIF + CXCL6 | MIF:CXCL6 |
| Three chemokines measured | |
| MIF + MIP1a + CXCL1 | MIF:MIP1a + MIF:CXCL1 |
| MIF + MIP1a + CXCL5 | MIF:MIP1a + MIF:CXCL5 |
| MIF + MIP1a + CXCL8 | MIF:MIP1a + MIF:CXCL8 |
| MIF + MIP1a + CXCL2 | MIF:MIP1a + MIF:CXCL2 |
| MIF + MIP1a + CXCL6 | MIF:MIP1a + MIF:CXCL6 |
| MIF + CXCL1 + CXCL5 | MIF:CXCL1 + MIF:CXCL5 |
| MIF + CXCL1 + CXCL8 | MIF:CXCL1 + MIF:CXCL8 |
| MIF + CXCL1 + CXCL2 | MIF:CXCL1 + MIF:CXCL2 |
| MIF + CXCL1 + CXCL6 | MIF:CXCL1 + MIF:CXCL6 |
| MIF + CXCL5 + CXCL8 | MIF:CXCL5 + MIF:CXCL8 |
| MIF + CXCL5 + CXCL2 | MIF:CXCL5 + MIF:CXCL2 |
| MIF + CXCL5 + CXCL6 | MIF:CXCL5 + MIF:CXCL6 |
| MIF + CXCL8 + CXCL2 | MIF:CXCL8 + MIF:CXCL2 |
| MIF + CXCL8 + CXCL6 | MIF:CXCL8 + MIF:CXCL6 |
| Four chemokines measured | |
| MIF + MIP1a + CXCL1 + CXCL5 | MIF:MIP1a + MIF:CXCL1 + MIF:CXCL5 |
| MIF + MIP1a + CXCL1 + CXCL8 | MIF:MIP1a + MIF:CXCL1 + MIF:CXCL8 |
| MIF + MIP1a + CXCL1 + CXCL2 | MIF:MIP1a + MIF:CXCL1 + MIF:CXCL2 |
| MIF + MIP1a + CXCL1 + CXCL6 | MIF:MIP1a + MIF:CXCL1 + MIF:CXCL6 |
| MIF + MIP1a + CXCL5 + CXCL8 | MIF:MIP1a + MIF:CXCL5 + MIF:CXCL8 |
| MIF + MIP1a + CXCL5 + CXCL2 | MIF:MIP1a + MIF:CXCL5 + MIF:CXCL2 |
| MIF + MIP1a + CXCL5 + CXCL6 | MIF:MIP1a + MIF:CXCL5 + MIF:CXCL6 |
| MIF + MIP1a + CXCL8 + CXCL2 | MIF:MIP1a + MIF:CXCL8 + MIF:CXCL2 |
| MIF + MIP1a + CXCL8 + CXCL6 | MIF:MIP1a + MIF:CXCL8 + MIF:CXCL6 |
| MIF + MIP1a + CXCL2 + CXCL6 | MIF:MIP1a + MIF:CXCL2 + MIF:CXCL6 |
| MIF + CXCL1 + CXCL5 + CXCL8 | MIF:CXCL1 + MIF:CXCL5 + MIF:CXCL8 |
| MIF + CXCL1 + CXCL5 + CXCL2 | MIF:CXCL1 + MIF:CXCL5 + MIF:CXCL2 |
| MIF + CXCL1 + CXCL5 + CXCL6 | MIF:CXCL1 + MIF:CXCL5 + MIF:CXCL6 |
| MIF + CXCL1 + CXCL8 + CXCL2 | MIF:CXCL1 + MIF:CXCL8 + MIF:CXCL2 |
| MIF + CXCL1 + CXCL8 + CXCL6 | MIF:CXCL1 + MIF:CXCL8 + MIF:CXCL6 |
| MIF + CXCL1 + CXCL2 + CXCL6 | MIF:CXCL1 + MIF:CXCL2 + MIF:CXCL6 |
| MIF + CXCL5 + CXCL8 + CXCL2 | MIF:CXCL5 + MIF:CXCL8 + MIF:CXCL2 |
| MIF + CXCL5 + CXCL8 + CXCL6 | MIF:CXCL5 + MIF:CXCL8 + MIF:CXCL6 |
| MIF + CXCL8 + CXCL2 + CXCL6 | MIF:CXCL8 + MIF:CXCL2 + MIF:CXCL6 |

TABLE 1-continued

Combinations of MIF plus one-six additional chemokines

| Chemokine levels quantified | Ratios calculated |
|---|---|
| Five chemokines measured | |
| MIF + MIP1a + CXCL1 + CXCL5 + CXCL8 | MIF:MIP1a + MIF:CXCL1 + MIF:CXCL5 + MIF:CXCL8 |
| MIF + MIP1a + CXCL1 + CXCL5 + CXCL2 | MIF:MIP1a + MIF:CXCL1 + MIF:CXCL5 + MIF:CXCL2 |
| MIF + MIP1a + CXCL1 + CXCL5 + CXCL6 | MIF:MIP1a + MIF:CXCL1 + MIF:CXCL5 + MIF:CXCL6 |
| MIF + MIP1a + CXCL5 + CXCL8 + CXCL2 | MIF:MIP1a + MIF:CXCL5 + MIF:CXCL8 + MIF:CXCL2 |
| MIF + MIP1a + CXCL5 + CXCL8 + CXCL6 | MIF:MIP1a + MIF:CXCL5 + MIF:CXCL8 + MIF:CXCL6 |
| MIF + MIP1a + CXCL5 + CXCL2 + CXCL6 | MIF:MIP1a + MIF:CXCL5 + MIF:CXCL2 + MIF:CXCL6 |
| MIF + MIP1a + CXCL8 + CXCL2 + CXCL6 | MIF:MIP1a + MIF:CXCL8 + MIF:CXCL2 + MIF:CXCL6 |
| MIF + CXCL1 + CXCL5 + CXCL8 + CXCL2 | MIF:CXCL1 + MIF:CXCL5 + MIF:CXCL8 + MIF:CXCL2 |
| MIF + CXCL1 + CXCL5 + CXCL8 CXCL6 | MIF:CXCL1 + MIF:CXCL5 + MIF:CXCL8 + MIF:CXCL6 |
| MIF + CXCL1 + CXCL8 + CXCL2 + CXCL6 | MIF:CXCL1 + MIF:CXCL8 + MIF:CXCL2 + MIF:CXCL6 |
| MIF + CXCL5 + CXCL8 + CXCL2 + CXCL6 | MIF:CXCL5 + MIF:CXCL8 + MIF:CXCL2 + MIF:CXCL6 |
| Seven chemokines measured | |
| MIF + MIP1a + CXCL1 + CXCL5 + CXCL8 + CXCL2 | MIF:MIP1a + MIF:CXCL1 + MIF:CXCL5 + MIF:CXCL8 + MIF:CXCL2 |
| MIF + MIP1a + CXCL1 + CXCL5 + CXCL8 + CXCL6 | MIF:MIP1a + MIF:CXCL1 + MIF:CXCL5 + MIF:CXCL8 + MIF:CXCL6 |
| MIF + CXCL1 + CXCL5 + CXCL8 + CXCL2 + CXCL6 | MIF:CXCL1 + MIF:CXCL5 + MIF:CXCL8 + MIF:CXCL2 + MIF:CXCL6 |
| Eight chemokines measured | |
| MIF + MIP1a + CXCL1 + CXCL5 + CXCL8 + CXCL2 + CXCL6 | MIF:MIP1a + MIF:CXCL1 + MIF:CXCL5 + MIF:CXCL8 + MIF:CXCL2 + MIF:CXCL6 |

The ratios MIF:MIP1a, MIF:CXCL1; MIF:CXCL5; MIF:CXCL8; MIF:CXCL2; and MIF:CXCL6 in gingival crevicular fluid are higher in individual's who have gingivitis than they are in healthy individuals because increased MIF levels and decreases levels of MIP1a, CXCL1, CXCL5, CXCL8, CXCL2 and CXCL6 are characteristic of gingivitis.

In some embodiments, the methods comprise quantifying MIF and MIP1a. In some embodiments, the ratio of MIF to MIP1a (MIF:MIP1a) is calculated and gingivitis is indicated if the MIF:MIP1a ratio above 5000, and the MIF level is above 10,000 and MIP1a is below 10. On the other hand, a healthy condition is indicated if the MIF:MIP1a ratio is above 5000, and MIF is equal or less than 10,000 and MIP1a is equal or less than 10.

Some embodiments related to method of treating an individual who has been identified as having gingivitis. Methods of treatment may comprise identifying the individual and then treating the individual for gingivitis. The individual may be identified by obtaining a sample of gingival crevicular fluid from the individual and evaluating the chemokine ratios present in the sample. MIF quantified together with one or more additional chemokines and one or more MIF to additional chemokine ratios is calculated. The one or more additional chemokines is selected from the group consisting of: MIP1a, CXCL1, CXCL5, CXCL8, CXCL2 and CXCL6; and the one or more ratios of MIF to additional chemokine is selected from the group consisting of: MIF:MIP1a, MIF:CXCL1; MIF:CXCL5; MIF:CXCL8; MIF:CXCL2; and MIF:CXCL6. In some embodiments, the one or more calculated MIF to additional chemokine ratios are compared to healthy reference ratios. The healthy reference ratios are ratios of the same chemokines in the calculated ratios. The healthy reference ratios are representative of ratios of an individual who does not have gingivitis. If the calculated ratio is greater than the healthy reference ratio, the individual is identified as having gingivitis. In some embodiments, the one or more calculated MIF to additional chemokine ratios are compared to gingivitis reference ratios. The gingivitis reference ratios are ratios of the same chemokines in the calculated ratios. The gingivitis reference ratios are representative of ratios of an individual who has gingivitis. If the calculated ratio is less than the gingivitis reference ratio, the individual is identified as not having gingivitis. In some embodiments, MIF and MIP1a are quantified and the MIF:MIP1a ratio is calculated. If the MIF:MIP1a ratio above 5000, and the MIF level is above 10,000 and MIP1a is below 10, the individual is identified as having gingivitis. If, the MIF:MIP1a ratio is above 5000, and MIF is equal or less than 10,000 and MIP1a is equal or less than 10, the individual is identified as not having gingivitis. Individuals identified as having gingivitis may be treated to resolve the gingivitis. In some embodiments, the individual who are identified as having gingivitis are treated by applying to the individual's oral cavity an oral care composition comprising one or more ingredients selected from the group consisting of: arginine, zinc phosphate, zinc oxide, zinc citrate, triclosan, chlorhexidine digluconate, thymol, menthol, eucalyptol, methyl salicylate, saline, antibiotics and fluoride. In some embodiments, the method comprises identifying the individual as having gingivitis by quantifying two, three, four, five or six additional chemokines in the sample and calculating two, three, four, five or six MIF to additional chemokine ratios. In some embodiments, the MIF and additional chemokines are quantified using a cytometric bead array, flow cytometry or ELISA spot assay.

Some embodiments related to method of monitoring an individual's response to treatment. The methods comprise at a first time point, obtaining a sample of gingival crevicular fluid from the individual and evaluating the chemokine ratios present in the sample. Then, after a period of time, at a second time point, obtaining a sample of gingival crevicular fluid from the individual and evaluating the chemokine ratios present in the sample. The results from the first time point are compared to the results from the second time point. In some embodiments, the individual is treated for gingivitis during the period of time between the first and second time points. In some embodiments, a sample of gingival crevicular fluid from the individual at a first time point and at a second time point. In some embodiments, a sample of gingival crevicular fluid from the individual at a first time point and two or more subsequence time points. The chemokine ratios present in the first time point sample, the second time point sample and any other subsequent time point sample are each evaluated, wherein for each time point, MIF is quantified together with one or more additional chemokines and one or more MIF to additional chemokine ratios is calculated. The one or more additional chemokines is selected from the group consisting of: MIP1a, CXCL1, CXCL5, CXCL8, CXCL2 and CXCL6; and the one or more ratios of MIF to additional chemokine is selected from the group consisting of: MIF:MIP1a, MIF:CXCL1; MIF:CXCL5; MIF:CXCL8; MIF:CXCL2; and MIF:CXCL6. In some embodiments, MIF and MIP1a are quantified and the MIF:MIP1a ratio is calculated. Individuals identified as having gingivitis may be treated to resolve the gingivitis. In some embodiments, for each time point the method comprises quantifying one two, three, four, five or six additional chemokines in the sample and calculating one, two, three, four, five or six MIF to additional chemokine ratios. In some embodiments, the MIF and additional chemokines are quantified using a cytometric bead array, flow cytometry or ELISA spot assay. In some embodiments, the individual is treated for gingivitis between time points by applying to the individual's oral cavity an oral care composition comprising one or more ingredients selected from the group consisting of: arginine, zinc phosphate, zinc oxide, zinc citrate, triclosan, chlorhexidine digluconate, thymol, menthol, eucalyptol, methyl salicylate, saline, antibiotics and fluoride. A reduction in MIF to other chemokine ratios from the results of a prior time point to results at a later time point indicate that the individual is shifting to a healthier state and gingivitis is being resolved.

EXAMPLES

Example 1

Gingivitis was successfully induced in human study subjects after 21 days of abstinence from oral hygiene as evidenced by a significant increase in gingival inflammation parameters. The chemokine analysis showed that only MIF (Macrophage Inhibitory Factor) significantly increased during the induction phase of the study whereas neutrophil chemokines MIP-1a, CXCL1, CXCL5, CXCL8, CXCL2 and CXCL6 decreased either initially after gingivitis induction or during the entire induction phase of gingivitis. The data demonstrate that a significant shift in host homeostasis occurs upon the onset of gingivitis with the majority of the response being suppression of host chemotactic factors for neutrophils.

Experimental Procedure

A stent induced biofilm overgrowth model of experimental gingivitis was employed in a split mouth design to take 21 patients through a 21 day induced gingivitis experiment. Each person served as their own control and used a standard fluoride dentifrice during hygiene implementation (washout and resolution). The gingival crevicular fluid (GCF), plaque and saliva were sampled before washout (Day −14), at baseline (Day 0), and at test days four (Day 4), seven (Day 7), fourteen (Day 14) and 21 (Day 21) of experimental gingivitis with days twenty-eight (Day 28) and thirty-five (Day 35) sampled for analysis of resolution factors. For GCF Sample collection, sites to be sampled are first be isolated with cotton rolls and gently air-dried. Paper strips (Periopaper; Oraflow Inc., Smithtown, N.Y., USA) or paper points (ISO 30) (Dentsply-De-Trey GmbH, Konstanz, Germany) are gently placed for 30 seconds into the pocket until a minimum of resistance is felt. Samples are eluted at 4° C. overnight into 500 µl phosphate buffered saline (PBS). After being centrifuged at 400 g for 4 min, the paper points/strips are removed; both paper points/strips and the supernatants are kept frozen at 20° C. until assayed. The GCF was analyzed for neutrophil chemokines, the plaque samples for microbiome analysis while the saliva was harvested for neutrophils. A Multiplex immunoassay for gingival crevicular fluid was used to detect neutrophil chemokines including MIF, MIP-1a, CXCL1, CXCL5, CXCL8, CXCL2 and CXCL6.

Results and Discussion

A total of twenty-one subjects were enrolled comprising of 10 females and 11 male participants aging between 18-35 years with mean age of 23.33 (median=22; standard deviation=4.37; standard error=0.95). All twenty-one participants completed the study and complied with study protocol with no reported adverse events. One subject missed one appointment at Day 7 due to family emergency.

The results showed no difference between test and control sides at baseline Day 0 in regard to clinical parameters. The data demonstrated a significant increase in all gingival inflammation parameters from baseline to Day 21 on the test side, which decrease back to baseline levels at Day 35 after reinstitution of oral hygiene measures. A significant change in clinical parameters was observed in the transition from health to disease. Consistent with findings from previous experimental gingivitis studies, during gingivitis induction in the present study, gingival index (GI), plaque index (PI), bleeding on probing (BOP) and gingival crevicular fluid (GCF) volume were statistically significantly higher in test side compared with control side.

Based on gingival inflammation severity determined by gingival index score on Day 21 using k-means clustering algorithm, a high responder group (16 subjects) and a low responder group (5 subjects) were identified in the 21 subject study population. The five low responders each had GI≤1.5 on day 21 while each of the sixteen high responders had GI≥1.8 at the same time point, which is consistent with clinically perceivable gingivitis.

Data was generated using the Multiplex immunoassay for gingival crevicular fluid to detect neutrophil chemokines including MIF, MIP-1a, CXCL1, CXCL5, CXCL8, CXCL2 and CXCL6. Data from the control side is shown in Table 2 below. Data from the test side is shown in Table 3 below. FIG. 1 shows control and test data side by side in bar graphs for the chemokines measured.

Only one neutrophil chemokine, macrophage migration inhibitory factory (MIF), which is the most abundant neutrophil chemokine found in GCF, was found to significantly increase during gingivitis induction in the test sides in comparison to control sides. It statistically significantly increased from baseline level (median=1557.62 pg/sample) to the first time point at Day 4 (median=4005.15 pg/sample), 2.6-fold increase, in the test side and remained elevated during the entire gingivitis period. It went back to baseline levels after gingivitis resolution (Day 28) and at the end of the study (Day 35). This neutrophil chemokine is known to be a central regulator of neutrophil function. Its expression is tightly coupled to gingivitis induction. MIF has been reported to increase in younger individuals and decrease in older individuals in a previous human gingivitis study.

In addition, at baseline (Day 0) a low responder group (identified at day 21) clearly separated from high responders in terms of their MIF levels, which were lower. MIF remains low for low responders when they return to health at the end study Day 35. None of the other chemokines showed such a clear association with clinical response; low GI responders had low MIF levels at baseline and at the end of the study.

The next three most abundant neutrophil chemokines at baseline (CXCL1; test side median=99.97 pg/sample and control side median=112.47 pg/sample: CXCL5; test side median=36.55 pg/sample and control side median=38.37 pg/sample: and IL-8 (CXCL8); test side median=156.83 pg/sample and control side median=155.83 pg/sample). CXCL1 and CXCL5 showed transient (Day 4 and 7) decrease in GCF levels in the test side. However, at Day 14, while the plaque index, gingival index, and BOP sites were still increasing the amount of these two chemokines returned to baseline levels. In contrast, IL-8 showed a decrease for the entire period of gingivitis. This is the first report of a reduction in the levels of CXCL1 during gingivitis induction. One previous report described a reduction in CXCL5 and two previous reports have described reduction in IL-8.

The next three most abundant chemokines (CXCL2; test side median=3.51 pg/sample and control side median=3.7 pg/sample: CXCL6; test side median=3.05 pg/sample and control side median=3.18 pg/sample: and MIP1a (CCL3); test side median=2.61 pg/sample and control side median=3.14 pg/sample) showed different expression patterns. CXCL2 demonstrated a transient decrease in GCF levels in stent area (reduced Day 4 and 7: restored to baseline at Day 14) as described for the CXCL1 and CXCL5. In contrast, CXCL6 and MIP1a showed a decrease for the entire period of gingivitis similar to IL-8.

Finally, with the two least abundant neutrophil chemokines (CXCL12; test side median=1.6 pg/sample and control side median=1.74 pg/sample; and CCL7; test side median=0.51 pg/sample and control side median=0.58 pg/sample) showed slight increase for the entire period of gingivitis induction in test side. However, due to low level of detection, data from those two chemokines might not have relevant significance.

Summary of Neutrophil Chemokine Findings

These data demonstrate that during the initial transition from clinical health to gingivitis a significant shift in chemokine utilization patterns occurs. In this experimental model, there is a significant increase in MIF, the most abundant neutrophil chemokine found in clinically healthy tissue, and significant decreases in the concentration of neutrophil chemokines MIP-1a, CXCL1, CXCL5, CXCL8, CXCL2 and CXCL6.

The data in Tables 2 and 3 is used to generate MIF: chemokine ratios and cut-offs for indication of healthy or gingivitis diagnosis is derived from a comparison of ratios from control side and test side.

Figure 2:
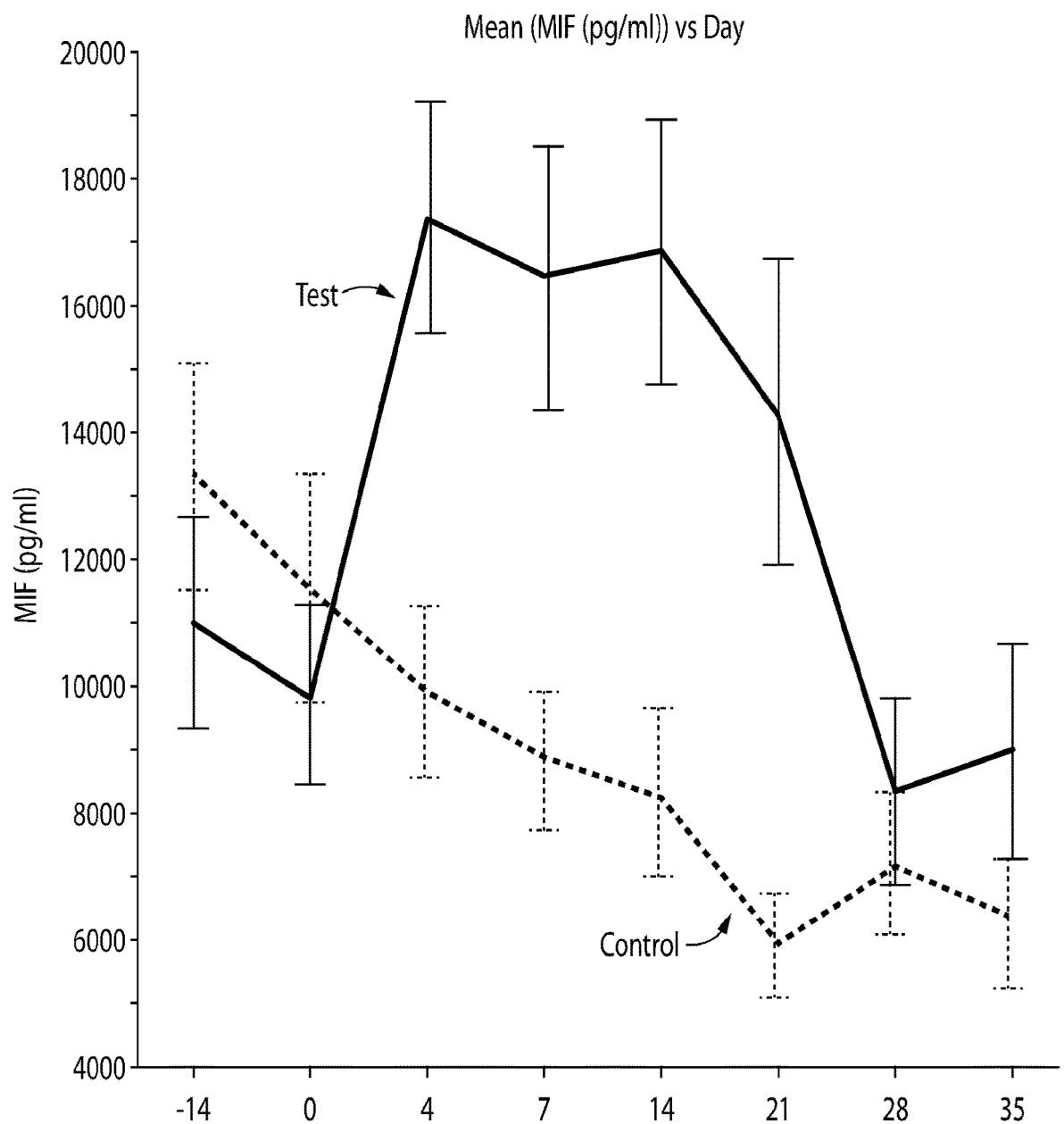
FIG. 2 shows MIF levels vs. Day from control (healthy) side and test (gingivitis) side from Example 1.

FIG. 2 shows MIF levels vs. Day from control (healthy) side and test (gingivitis) side.

Figure 3:
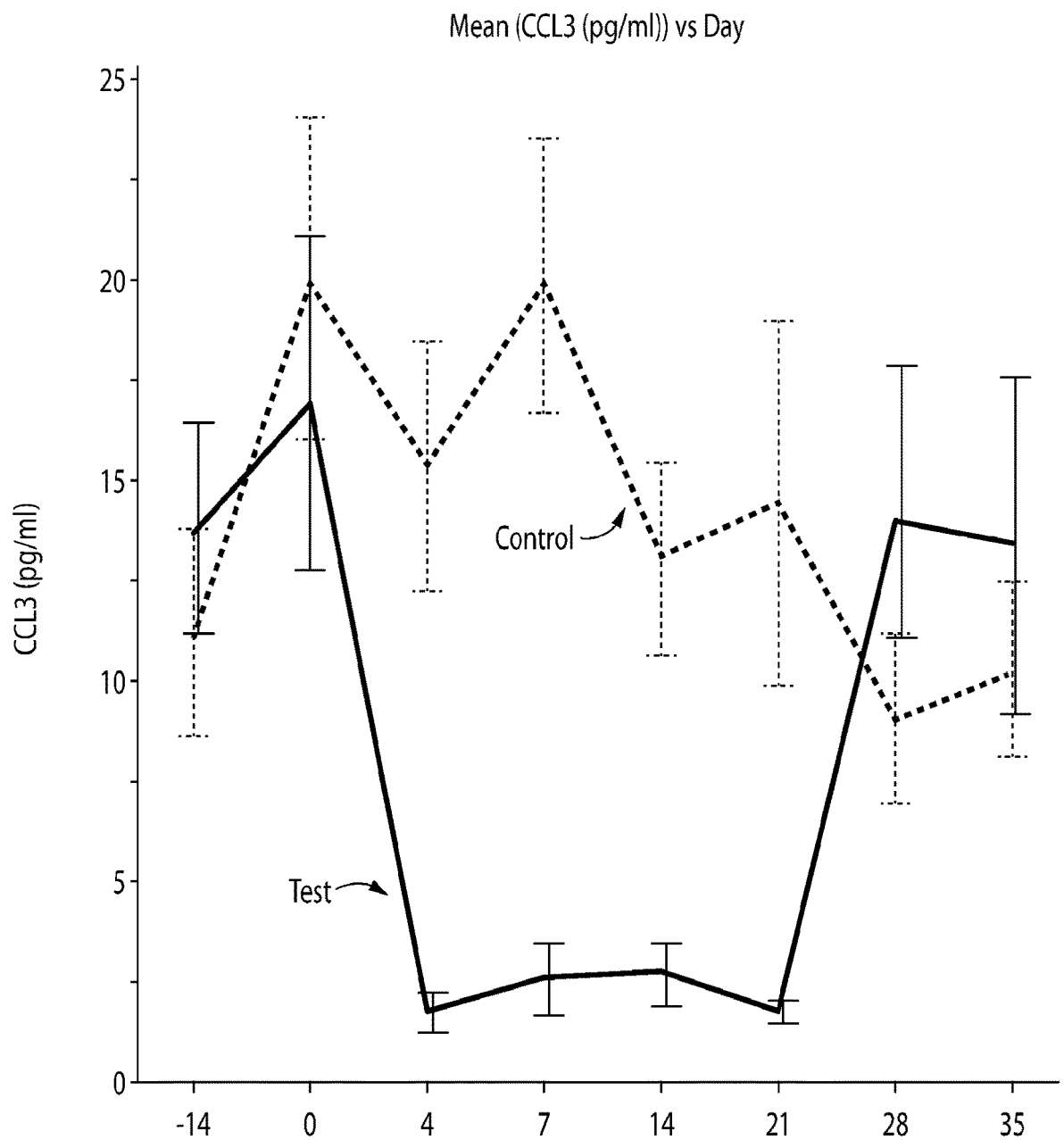
FIG. 3 shows MIP1a levels vs. Day from control (healthy) side and test (gingivitis) side from Example 1.

FIG. 3 shows MIP1a levels vs. Day from control (healthy) side and test (gingivitis) side.

Figure 4:
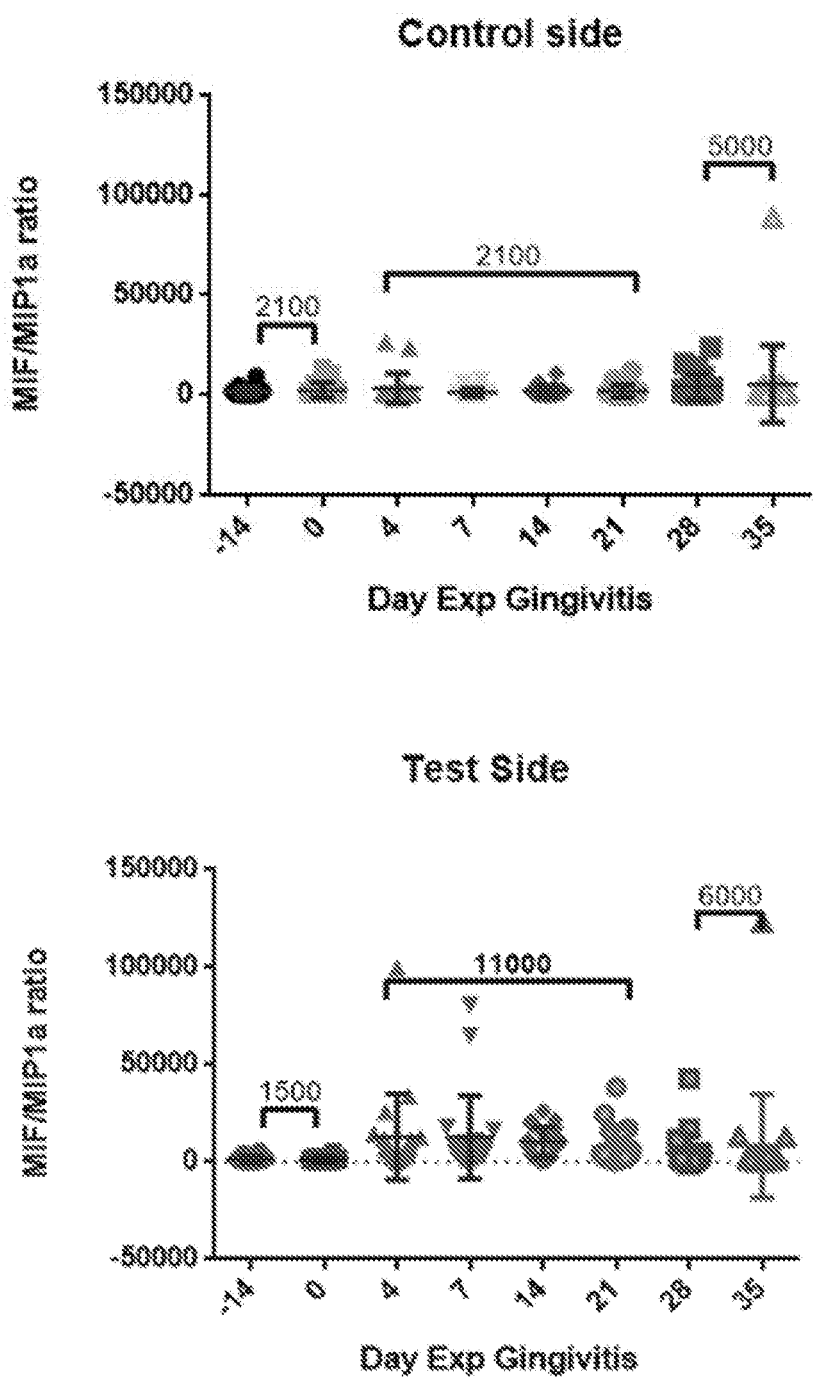
FIG. 4 shows MIF/MIP1a ratios from control (healthy) side and test (gingivitis) side at each time point of the study in Example 1.

FIG. 4 shows MIF/MIP1a ratios from control (healthy) side and test (gingivitis) side at each time point of the study. Throughout the test days (Days 4, 7, 14 and 21) the MIF:MIP1a ratio on the control side was about 2000 while the MIF:MIP1a ratio on the test side was about 11,000. A MIF:MIP1a ratio of below 5000 may indicate healthy. A MIF:MIP1a ratios of greater than 5000 in which the MIF level is above 10,000 and MIP1a is below 10 is indicative of gingivitis while a MIF:MIP1a ratio greater than 5000 in which MIF is equal or less than 10,000 and MIP1a is equal or less than 10, in indicative of not having gingivitis.

TABLE 2

Control Side Data-Median levels of chemokines total amount expressed in pg/sample during different study visits.

| Chemokine total amount Median (pg/sample) | N | Baseline Day -14 | Day 0 | Control Induction Day 4 | Day 7 | Day 14 | Day 21 | Resolution Day 28 | Day 35 |
|---|---|---|---|---|---|---|---|---|---|
| CCL21 | 282 | 2.732 | 2.732 | 3.281 | 3.671 | 3.37 | 2.154 | 1.948 | 2.026 |
| CXCL13 | 332 | 0.39 | 0.656 | 0.35 | 0.516 | 0.486 | 0.36 | 0.4 | 1.316 |
| CCL27* | 153 | 0.156 | 0.153 | 0.059 | 0.093 | 0.038 | 0.088 | 0.076 | 0.082 |
| CXCL5 | 269 | 43.57 | 38.374 | 39.664 | 45.476 | 30.678 | 33.594 | 29.878 | 32.66 |
| CCL11 | 266 | 0.48 | 0.532 | 0.48 | 0.494 | 0.521 | 0.118 | 0.406 | 0.422 |
| CCL24 | 101 | 0.804 | 0.563 | 0.908 | 0.767 | 0.96 | 0.99 | 0.639 | 0.397 |
| CCL26 | 129 | 0.062 | 0.066 | 0.056 | 0.084 | 0.046 | 0.062 | 0.06 | 0.063 |
| CX3CL1 | 326 | 2.234 | 1.47 | 1.86 | 1.767 | 1.444 | 1.828 | 7.23 | 1.378 |
| CXCL6 | 333 | 3.47 | 3.182 | 3.412 | 4.953 | 3.196 | 2.516 | 2.67 | 2.468 |
| GM_CSF | 298 | 3.448 | 3.06 | 3.05 | 3.01 | 3.518 | 2.974 | 3.005 | 3.004 |
| CXCL1 | 334 | 127.782 | 172.468 | 115.492 | 130.555 | 100.838 | 98.532 | 77.09 | 85.414 |
| CXCL2 | 328 | 1.278 | 3.704 | 1.202 | 4.659 | 3.212 | 3.405 | 2.223 | 3.814 |
| CCL1 | 234 | 0.98 | 7.206 | 1.104 | 1.067 | 1.056 | 0.672 | 0.806 | 0.739 |
| IFN y | 236 | 0.13 | 0.16 | 0.163 | 0.204 | 0.127 | 0.128 | 0.1 | 0.056 |
| IL_1b | 334 | 11.006 | 22.694 | 17.072 | 29.024 | 13.426 | 13.572 | 13.612 | 13.402 |
| IL 2 | 204 | 0.048 | 0.05 | 0.072 | 0.054 | 0.061 | 0.032 | 0.048 | 0.05 |
| IL 4 | 55 | 0.143 | 0.056 | 0.136 | 0.239 | 0.116 | 0.198 | 0.104 | 0.091 |
| IL_6 | 299 | 0.466 | 0.473 | 0.34 | 0.361 | 0.272 | 0.166 | 0.26 | 0.3 |
| IL_8 | 334 | 129.91 | 155.828 | 148.812 | 204.236 | 149.246 | 101.38 | 86.438 | 81.414 |
| IL_10 | 309 | 0.593 | 0.558 | 0.504 | 0.52 | 0.36 | 0.405 | 0.328 | 0.288 |
| IL_16 | 334 | 61.186 | 53.018 | 67.404 | 60.191 | 25.368 | 39.01 | 37.014 | 37.206 |
| CXCL10 | 316 | 0.846 | 0.928 | 1.11 | 0.994 | 0.952 | 0.716 | 9.976 | 0.766 |
| CXCL11 | 152 | 0.082 | 0.076 | 0.055 | 0.056 | 0.051 | 0.117 | 0.03 | 0.054 |
| CCL2 | 333 | 0.242 | 0.43 | 0.388 | 0.323 | 0.25 | 0.17 | 0.176 | 0.152 |
| CCL8 | 258 | 0.049 | 0.126 | 0.084 | 0.113 | 0.084 | 0.029 | 0.057 | 0.05 |
| CCL7 | 225 | 0.533 | 0.576 | 0.656 | 0.576 | 0.585 | 0.468 | 0.514 | 0.514 |

TABLE 2-continued

Control Side Data-Median levels of chemokines total amount expressed in pg/sample during different study visits,

| Chemokine total amount Median (pg/sample) | N | Baseline | | Control Induction | | | | Resolution | |
|---|---|---|---|---|---|---|---|---|---|
| | | Day -14 | Day 0 | Day 4 | Day 7 | Day 14 | Day 21 | Day 28 | Day 35 |
| CCL13 | 333 | 1.094 | 0.95 | 0.856 | 0.784 | 0.69 | 0.628 | 0.558 | 0.57 |
| CCL22 | 278 | 0.523 | 0.557 | 0.504 | 0.84 | 0.609 | 0.54 | 0.554 | 0.501 |
| MIF | 334 | 2483.786 | 1705.416 | 1976.364 | 1716.889 | 1524.012 | 1014.538 | 1217.51 | 1061.572 |
| CXCL9 | 317 | 6.778 | 6.96 | 6.108 | 7.906 | 5.42 | 4.348 | 6.087 | 6.344 |
| CCL3 | 331 | 1.294 | 3.144 | 2.338 | 3.56 | 1.96 | 1.653 | 1.022 | 1.036 |
| CCL15 | 324 | 1.208 | 7.312 | 1.104 | 1.158 | 1.358 | 0.925 | 0.919 | 0.791 |
| CCL20 | 320 | 0.61 | 0.518 | 0.488 | 0.666 | 0.463 | 0.386 | 0.304 | 0.496 |
| CCL19 | 272 | 0.454 | 0.43 | 0.35 | 0.521 | 0.422 | 0.372 | 0.358 | 0.464 |
| CCL23 | 191 | 0.178 | 0.170 | 0.183 | 0.157 | 0.181 | 0.14 | 0.108 | 0.139 |
| CXCL16 | 331 | 0.782 | 7.124 | 0.65 | 0.971 | 0.764 | 0.479 | 0.49 | 0.506 |
| CXCL12 | 155 | 2.027 | 7.742 | 2.019 | 1.625 | 2.376 | 1.43 | 1.532 | 1.204 |
| CCL17 | 42 | 0.398 | 0.463 | 0.276 | 0.288 | 0.461 | 0.366 | 0.374 | 0.298 |
| CCL25 | 332 | 6.516 | 6.589 | 6.516 | 5.593 | 5.488 | 3.73 | 4.936 | 4.356 |
| TNF_a | 329 | 0.49 | 0.676 | 0.534 | 0.898 | 0.676 | 0.306 | 0.4 | 0.36 |

TABLE 3

Test Side Data-Median levels of chemokines total amount expressed in pg/sample during different study visits,

| Baseline | | Test Induction | | | | Resolution | |
|---|---|---|---|---|---|---|---|
| Day -14 | Day 0 | Day 4 | Day 7 | Day 14 | Day 21 | Day 28 | Day 35 |
| 2.31 | 2.692 | 1.99 | 2.396 | 2.356 | 2.17 | 3.408 | 2.94 |
| 0.47 | 0.56 | 0.36 | 0.372 | 0.326 | 0.278 | 0.359 | 0.372 |
| 0.104 | 0.114 | 0.088 | 0.109 | 0.081 | 0.062 | 0.128 | 0.041 |
| 41.916 | 36.545 | 32.204 | 26.73 | 37.064 | 32.914 | 41.301 | 33.593 |
| 0.519 | 0.518 | 0.117 | 0.318 | 0.466 | 0.364 | 0.494 | 0.422 |
| 1.016 | 1.28 | 0.766 | 0.272 | 1.005 | 0.543 | 0.802 | 0.652 |
| 0.043 | 0.045 | 0.042 | 0.052 | 0.046 | 0.068 | 0.074 | 0.032 |
| 2.218 | 1.442 | 1.864 | 1.111 | 2.032 | 1.77 | 1.851 | 1.282 |
| 3.63 | 3.052 | 1.868 | 2.529 | 2.156 | 1.6 | 3.112 | 2.68 |
| 8.046 | 3.009 | 2.814 | 2.402 | 3.03 | 2.734 | 3.1 | 3.166 |
| 122.56 | 99.974 | 87.44 | 84.244 | 109.718 | 106.2 | 105.26 | 99.734 |
| 4.502 | 3.51 | 1.764 | 2.564 | 3.898 | 3.684 | 3.796 | 3.452 |
| 1.175 | 1.096 | 0.954 | 0.954 | 0.862 | 0.698 | 0.811 | 1.054 |
| 0.118 | 0.118 | 0.096 | 0.103 | 0.16 | 0.128 | 0.191 | 0.149 |
| 16.456 | 20.628 | 13.146 | 22.398 | 47.13 | 35.524 | 13.75 | 19.762 |
| 0.068 | 0.05 | 0.039 | 0.028 | 0.053 | 0.045 | 0.04 | 0.067 |
| 0.116 | 0.076 | . | . | 0.17 | 0.018 | 0.069 | 0.062 |
| 0.436 | 0.353 | 0.09 | 0.082 | 0.123 | 0.078 | 0.484 | 0.294 |
| 127.776 | 158.825 | 72.388 | 67.545 | 94.912 | 74.784 | 157.412 | 100.154 |
| 0.612 | 0.474 | 0.538 | 0.424 | 0.484 | 0.318 | 0.444 | 0.479 |
| 42.238 | 41.256 | 28.094 | 27.142 | 36.89 | 50.93 | 44.05 | 36.884 |
| 0.804 | 0.82 | 0.786 | 0.61 | 0.8 | 0.586 | 1.19 | 0.845 |
| 0.061 | 0.074 | 0.03 | 0.134 | 0.044 | 0.07 | 0.054 | 0.092 |
| 0.332 | 0.262 | 0.132 | 0.134 | 0.164 | 0.104 | 0.332 | 0.124 |
| 0.087 | 0.07 | 0.022 | 0.014 | 0.028 | 0.012 | 0.083 | 0.036 |
| 0.582 | 0.514 | 0.56 | 0.602 | 0.662 | 0.674 | 0.55 | 0.485 |
| 1.084 | 0.626 | 0.83 | 0.572 | 0.744 | 0.638 | 0.734 | 0.695 |
| 0.524 | 0.472 | 0.765 | 0.856 | 0.975 | 0.454 | 0.706 | 0.372 |
| 1788.59 | 1557.618 | 4005.154 | 3531.738 | 3384.47 | 2568.388 | 1459.618 | 1391.94 |
| 4.762 | 4.794 | 3.306 | 2.702 | 5.04 | 3.21 | 8.985 | 4.166 |
| 1.804 | 2.609 | 0.226 | 0.31 | 0.322 | 0.362 | 1.556 | 1.314 |
| 1.372 | 1.008 | 1.253 | 1.103 | 1.732 | 1.674 | 1.362 | 0.959 |
| 0.656 | 0.453 | 0.322 | 0.234 | 0.466 | 0.308 | 0.595 | 0.345 |
| 0.456 | 0.408 | 0.416 | 0.478 | 0.386 | 0.286 | 0.4 | 0.486 |
| 0.265 | 0.258 | 0.09 | 0.144 | 0.138 | 0.221 | 0.204 | 0.193 |
| 0.744 | 0.832 | 0.708 | 0.664 | 1.01 | 0.622 | 0.847 | 0.795 |
| 1.71 | 1.595 | 1.67 | 1.532 | 2.176 | 2.009 | 2.042 | 1.44 |
| 0.337 | 0.409 | 0.407 | 0.366 | 0.384 | 0.346 | 0.425 | 0.466 |
| 6.48 | 5.636 | 10.638 | 9.332 | 7.158 | 6.424 | 4.976 | 5.354 |
| 0.604 | 0.528 | 0.249 | 0.275 | 0.53 | 0.395 | 0.718 | 0.412 |

The invention claimed is:

1. A method of determining one or more ratios of chemokines in gingival crevicular fluid of an individual selected from the group consisting of: MIF:MIP1a, MIF:CXCL1; MIF:CXCL5; MIF:CXCL8; MIF:CXCL2; and MIF:CXCL6; the method comprising the steps of:
  obtaining a sample of gingival crevicular fluid from the individual;
  quantifying Macrophage migration Inhibitory Factor (MIF) in the sample;
  quantifying one or more additional chemokines in the sample and calculating one or more MIF to additional chemokine ratios, wherein the one or more chemokines is selected from the group consisting of: Macrophage Inflammatory Protein 1a (MIP1a), C-X-C motif chemokine ligand 1 (CXCL1), C-X-C motif chemokine ligand 5 (CXCL5), Interleukin 8 (CXCL8) C-X-C motif chemokine ligand 2 (CXCL2), and C-X-C motif chemokine ligand 6 (CXCL6), and the one or more ratios of MIF to additional chemokines is selected from the group consisting of: MIF:MIP1a, MIF:CXCL1; MIF:CXCL5; MIF:CXCL8; MIF:CXCL2; and MIF:CXCL6.

2. The method of claim 1 wherein MIP1a is quantified and the ratio MIF:MIP1a is calculated.

3. The method of claim 1 wherein two, three, four, five or six additional chemokines in the sample are quantified and two, three, four, five or six MIF to additional chemokine ratios are calculated.

4. The method of claim 1 wherein the MIF and additional chemokines are quantified using a cytometric bead array, flow cytometry or ELISA spot assay.

5. A method of treating an individual who has gingivitis comprising the steps of:
  a) identifying the individual as having gingivitis by
    i) obtaining a sample of gingival crevicular fluid from the individual;
    ii) quantifying Macrophage migration Inhibitory Factor (MIF) in the sample;
    iii) quantifying one or more additional chemokines in the sample, wherein the one or more additional chemokines is selected from the group consisting of: Macrophage Inflammatory Protein 1a (MIP1a), C-X-C motif chemokine ligand 1 (CXCL1), C-X-C motif chemokine ligand 5 (CXCL5), Interleukin 8 (CXCL8), C-X-C motif chemokine ligand 2 (CXCL2) and C-X-C motif chemokine ligand 6 (CXCL6);
    iv) calculating one or more calculated ratios selected from the group consisting of: MIF:MIP1a, MIF:CXCL1; MIF:CXCL5; MIF:CXCL8; MIF:CXCL2; and MIF:CXCL6; and
    v) comparing the one or more calculated ratios to healthy reference ratios of MIF to the same additional chemokines, wherein said healthy reference ratios exist in an individual not having gingivitis and a calculated ratio greater than the healthy reference ratio indicates the individual has gingivitis; and
  b) applying to the individual's oral cavity an oral care composition comprising one or more ingredients selected from the group consisting of: arginine, zinc phosphate, zinc oxide, zinc citrate, triclosan, chlorhexidine digluconate, thymol, menthol, eucalyptol, methyl salicylate, saline, antibiotics and fluoride.

6. A method of monitoring the treatment an individual who has gingivitis comprising the steps of:
  a) determining one or more ratios of chemokines in gingival crevicular fluid of an individual selected from the group consisting of: MIF:MIP1a, MIF:CXCL1; MIF:CXCL5; MIF:CXCL8; MIF:CXCL2; and MIF:CXCL6 by
    i) obtaining a sample of gingival crevicular fluid from the individual;
    ii) quantifying Macrophage migration Inhibitory Factor (MIF) in the sample;
    iii) quantifying one or more additional chemokines in the sample, wherein the one or more additional chemokines is selected from the group consisting of: Macrophage Inflammatory Protein 1a (MIP1a), C-X-C motif chemokine ligand 1 (CXCL1), C-X-C motif chemokine ligand 5 (CXCL5), Interleukin 8 (CXCL8), C-X-C motif chemokine ligand 2 (CXCL2) and C-X-C motif chemokine ligand 6 (CXCL6);
    iv) calculating one or more ratios selected from the group consisting of: MIF:MIP1a, MIF:CXCL1; MIF:CXCL5; MIF:CXCL8; MIF:CXCL2; and MIF:CXCL6;
  b) treating the individual by applying to the individual's oral cavity an oral care composition comprising one or more ingredients selected from the group consisting of: arginine, zinc phosphate, zinc oxide, zinc citrate, triclosan, chlorhexidine digluconate, thymol, menthol, eucalyptol, methyl salicylate, saline, antibiotics and fluoride; and
  c) repeating step a), wherein a decrease in the same chemokine ratios indicates effective treatment.

7. The method of claim 6 wherein the MIF and additional chemokines are quantified using a cytometric bead array, flow cytometry or ELISA spot assay.

8. The method of claim 6 wherein MIP1a is quantified and the ratio MIF:MIPa is calculated.

9. The method of claim 8 wherein the MIF and MIP1a are quantified using a cytometric bead array, flow cytometry or ELISA spot assay.

10. The method of claim 5 wherein the MIF and additional chemokines are quantified using a cytometric bead array, flow cytometry or ELISA spot assay.

11. The method of claim 5 wherein MIP1a is quantified and the ratio MIF:MIPa is calculated.

12. The method of claim 11 wherein the MIF and MIP1a are quantified using a cytometric bead array, flow cytometry or ELISA spot assay.

* * * * *